(12) United States Patent
Pagano

(10) Patent No.: US 11,774,406 B2
(45) Date of Patent: Oct. 3, 2023

(54) ADVANCED HIGHSPEED SYSTEM TO IDENTIFY AND CLASSIFY AREAS OF RAIL ANOMALIES

(71) Applicant: Dominick A. Pagano, Naples, FL (US)

(72) Inventor: Dominick A. Pagano, Naples, FL (US)

(73) Assignee: Plasser American Corporation, Chesapeake, VA (US)

( * ) Notice: Subject to any disclaimer, the term of this patent is extended or adjusted under 35 U.S.C. 154(b) by 93 days.

(21) Appl. No.: 17/487,175

(22) Filed: Sep. 28, 2021

(65) Prior Publication Data

US 2022/0099630 A1 Mar. 31, 2022

Related U.S. Application Data

(60) Provisional application No. 63/084,042, filed on Sep. 28, 2020.

(51) Int. Cl.
*G01N 29/07* (2006.01)
*B61K 9/08* (2006.01)
*G01N 29/265* (2006.01)
*G01N 29/22* (2006.01)
(Continued)

(52) U.S. Cl.
CPC .............. *G01N 29/07* (2013.01); *B61K 9/08* (2013.01); *G01N 29/043* (2013.01); *G01N 29/225* (2013.01); *G01N 29/265* (2013.01); *G01N 33/2045* (2019.01); *G01N 2291/011* (2013.01); *G01N 2291/0234* (2013.01); *G01N 2291/0289* (2013.01); *G01N 2291/044* (2013.01);
(Continued)

(58) Field of Classification Search
CPC .... G01N 29/07; G01N 29/043; G01N 29/225; G01N 29/265; G01N 33/2045; G01N 29/2418; G01N 2291/044; G01N 2291/011; G01N 2291/0289; G01N 2291/0234; G01N 2291/106; G01N 2291/2623; B61K 9/08; B61L 23/045
USPC ........................................................... 73/598
See application file for complete search history.

(56) References Cited

U.S. PATENT DOCUMENTS 6,516,668 B2 *  2/2003  Havira ................... G01B 17/00
                                                        73/639
6,604,421 B1 *  8/2003  Li ............................ B61K 9/10
                                                        73/636
(Continued)

OTHER PUBLICATIONS

IEEE Transactions on Ultrasonics, Ferroelectrics, and Frequency Control, vol. 45, No. 1, Jan. 1998 Synthetic Aperture Techniques with a Virtual Source Element , Frazier et al. (Year: 1998).*

(Continued)

*Primary Examiner* — Jacques M Saint Surin
(74) *Attorney, Agent, or Firm* — Danielle C. Sullivan; Carter Ledyard & Milburn LLP

(57) ABSTRACT

The present invention provides a highspeed advanced system to identify and classify the area of anomalies in a railroad rail. This is achieved by using a novel linear array solution that employs parallel transmission of an ultrasonic beam and the use of a virtual synthetic aperture to receive reflected echoes. This integrated system has the capability to locate and classify near surface horizontal defects at speeds more than 40 km/h and at the same time maintaining a constant pulse density of at least 4 mm or less per incremental longitudinal movement.

11 Claims, 7 Drawing Sheets
(5 of 7 Drawing Sheet(s) Filed in Color)

(51) Int. Cl.
*G01N 33/2045* (2019.01)
*G01N 29/04* (2006.01)

(52) U.S. Cl.
CPC ............... *G01N 2291/106* (2013.01); *G01N 2291/2623* (2013.01)

(56) References Cited

U.S. PATENT DOCUMENTS

| | | | |
|---|---|---|---|
| 7,654,143 B2* | 2/2010 | Roney | G01N 29/44 |
| | | | 73/620 |
| 9,010,186 B2* | 4/2015 | Pagano | G01N 29/2493 |
| | | | 73/636 |
| 9,526,475 B2* | 12/2016 | Specht | A61B 8/463 |
| 10,342,518 B2* | 7/2019 | Specht | A61B 8/4483 |
| 10,724,998 B2* | 7/2020 | Standop | B61L 15/0072 |
| 10,766,510 B1* | 9/2020 | Pagano | G01N 29/069 |
| 11,161,531 B2* | 11/2021 | Sela | G01N 29/265 |
| 2004/0003662 A1* | 1/2004 | Kenderian | G01N 29/12 |
| | | | 73/579 |
| 2006/0065055 A1* | 3/2006 | Barshinger | G01N 29/262 |
| | | | 73/609 |
| 2015/0359512 A1* | 12/2015 | Boctor | G01S 15/8997 |
| | | | 600/447 |
| 2018/0202977 A1* | 7/2018 | Standop | G01N 29/0645 |

OTHER PUBLICATIONS

Virtual source aperture imaging for nondestructive testing, Nondestructive Testing and Condition monitoring, vol. 54, No. 7, Jul. 2012, The British Institute of Non-Destructive Testing (Year: 2012).*

* cited by examiner

ADVANCED HIGHSPEED SYSTEM TO IDENTIFY AND CLASSIFY AREAS OF RAIL ANOMALIES

This application claims priority to U.S. Provisional Patent Application No. 63/084,042, filed Sep. 28, 2020, entitled "Advanced High-speed System to Identify and Classify Areas of Rail Anomalies", and is hereby incorporated by reference in its entirety.

U.S. Pat. No. 10,766,510 (510 patent) is related to this application and is hereby incorporated by reference in its entirety.

The present invention relates to a method and apparatus for the ultrasonic inspection of test material, and more specifically, the ultrasonic inspection of railroad rails to detect cracks that propagate in the horizontal plane of the rail and longitudinally along the rail caused by Rolling Contact Fatigue. (RCF)

BACKGROUND OF THE INVENTION

The teachings in U.S. Pat. No. 10,766,510 improved the detection of horizontal defects located across the rail head near the surface and in the plastic zone area on the gauge corner of rails. Horizontal split head defects are the horizontal progressive defect originating inside of the rail head and are typically one ¼ inch or more below the running surface and progress horizontally in all directions. Such defects generally are initiated in the gauge and field side of the rail head, an area that was generally not inspected. The invention in the '510 patent advantageously directs the ultrasonic beams across the head and perpendicular to the surface of the rail to detect and classify such horizontal cracks.

Related to horizontal split head defects, but requiring a different detection method, are defects caused by Rolling Contact Fatigue. (RCF). RCF is a pervasive and insidious problem on all types of railway systems. The cracks caused by RCF are typically only a few millimeters apart and initially 1 to 2 mm deep. As the initial cracks are small, they are difficult to detect, but if not detected early the RCF cracks can readily grow to a size that will lead to service failures, broken rails, and/or derailments. Another problem is that current methods to detect such defects used conventional and linear phased arrays to sequentially scan across the rail head as the arrays travel longitudinally along the rail. This current method requires that the testing vehicle moving longitudinally along the rail is limited to a speed of 1.5-2 km/h, resulting in an extremely slow, and therefore an extremely expensive testing procedure.

It is an object of the present invention to provide a high-speed advanced inspection system to identify and classify the area of anomalies in railroad rails.

It is a further object of the present invention to provide a high-speed advanced inspection system to detect railroad rail anomalies caused by Rolling Contact Fatigue.

It is another object of the present invention to provide a high-speed advanced inspection system to detect railroad rail anomalies that allows the inspection vehicle to move along the railroad rail at speeds of more than 40 km/h.

It is a further object of the present invention to provide a high-speed advanced inspection system that detects railroad rail anomalies caused by Rolling Contact Fatigue and allows the inspection vehicle to move along the railroad rail at speeds more than 40 km/h.

It is a further object of the present invention to provide a high-speed advanced inspection system with the ability to locate and classify defects caused by Rolling Contact Fatigue and thereby provide railways an early detection system allowing proactive implementation of a preventive maintenance program.

SUMMARY OF THE INVENTION

The invention described herein provides for the use of a plurality of individual transducers, linear array transducers and phased array transducers for the detection of cracks that propagate in the horizontal plane of the rail and longitudinally along the rail. These defects are caused by many closely spaced surface cracks, only a few millimeters apart that occur as a result of Rolling Contact Fatigue, the process in which cracks are created as a result of the contact stresses between a rolling wheel and the rail. RCF defects are initiated at the rail surface and develop into the rail at an angle of about 20° to the running surface. The incremental growth of a crack or a series of cracks develop into near surface horizontal defects, and as they merge, they will eventually spawn Detail Fracture Defects in other areas of the rail head in and away from the gauge corner and can cause service failures and derailments.

Currently the state of the art in conventional linear and phased arrays consist of sequentially scanning across the rail head as the arrays travel longitudinally along the rail. As an example, to scan approximately 45 mm across the head of the rail utilizing a 32-element array, and obtain the needed resolution, will generally require 24 to 28 single individual pulse grouping across the width of the transducer before incrementally moving 4 mm to the next position. This limits the testing speed to 1.5-2 km/h.

The present invention provides a highspeed advanced system to identify and classify the area of each anomaly. This is achieved by using a novel linear array solution that employs parallel transmission of an ultrasonic beam and the use of a virtual synthetic aperture to receive reflected echoes. This integrated system has the capability to locate and classify near surface horizontal defects at speeds more than 40 km/h and at the same time maintaining a constant pulse density of at least 4 mm or less per incremental longitudinal movement.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further objects, features and advantages of the invention will become apparent from the following detailed description taken in conjunction with the accompanying figures showing illustrative embodiments of the invention, in which.

DETAILED DESCRIPTION OF THE INVENTION

Figure 1:
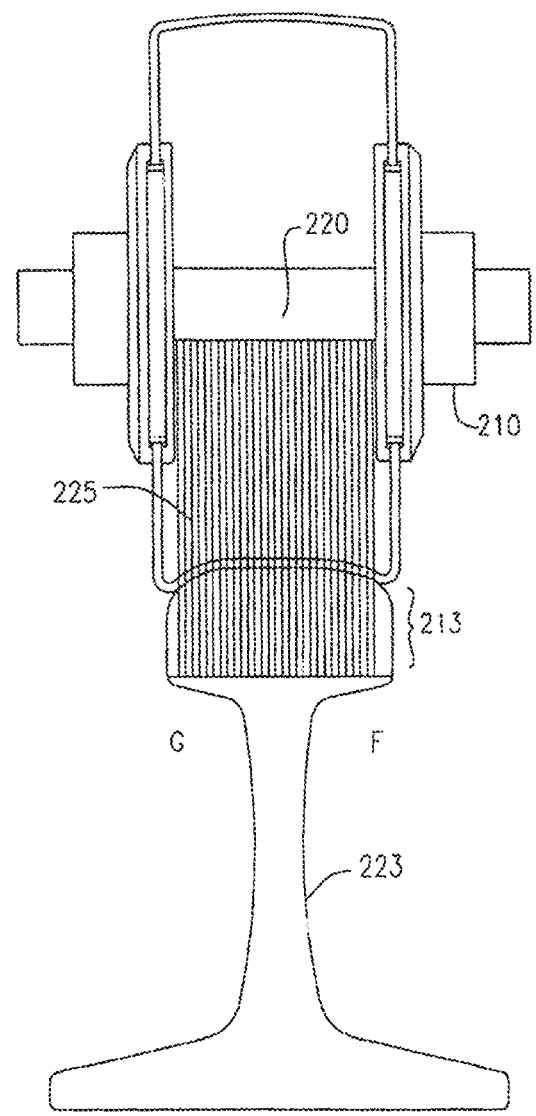
FIG. 1 Illustrates an ultrasonic linear array wheel on the rail with no defects present FIG. 2 Illustrates an ultrasonic linear array wheel on the rail with defects present FIG. 3 Illustrates the pulsing sequence of a 32-element linear array.
Figure 2:
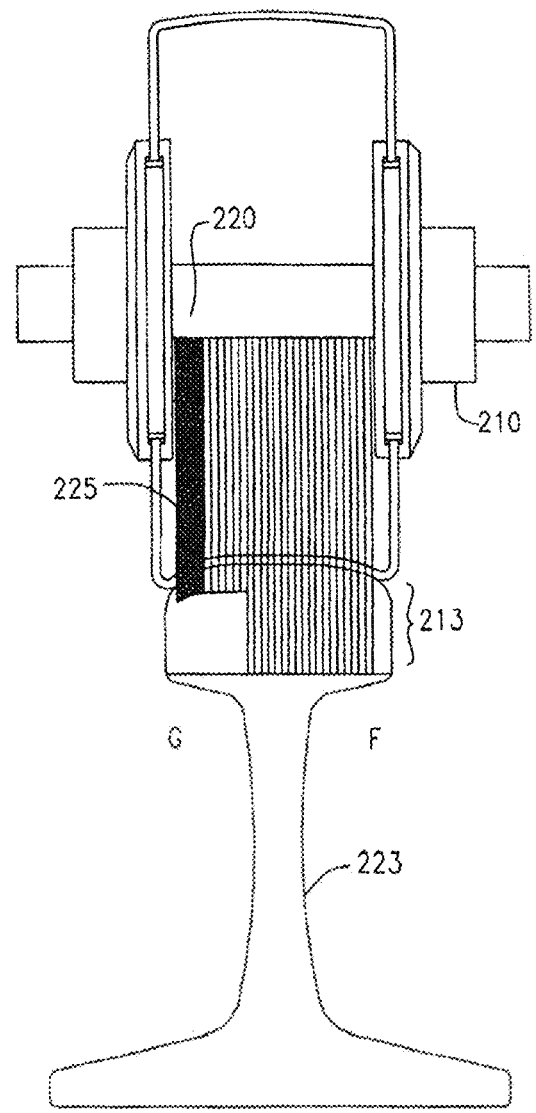

FIGS. 1 and 2 illustrate an ultrasonic rail detection system according to U.S. Pat. No. 10,766,510. The detection system shown in FIGS. 1 and 2 is also used in accordance with the present invention described herein.

Figure 4:
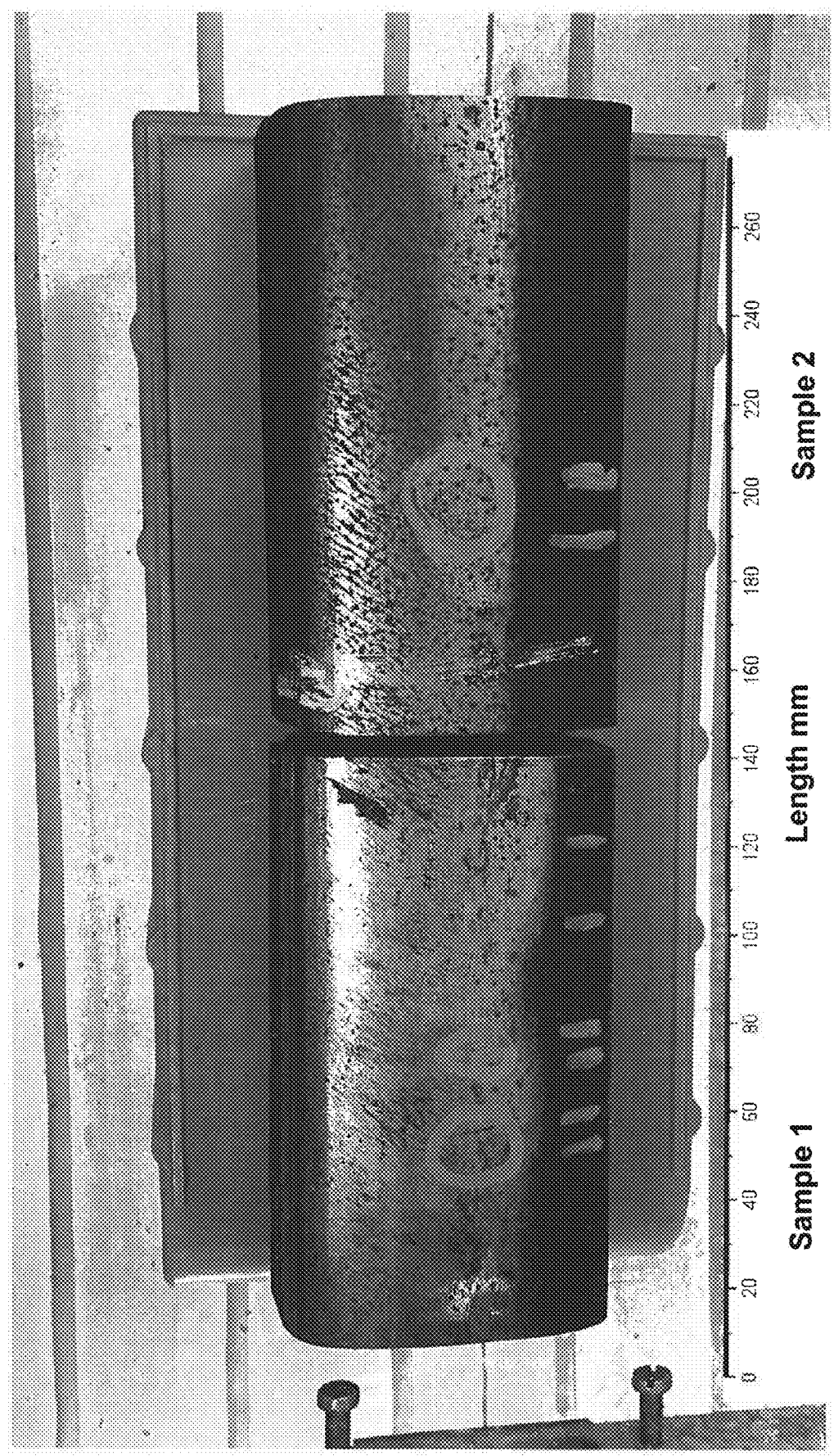
FIG. 4 Illustrates two Samples with identified and marked subsurface defects.

While the present invention embodies similar apparatus for performing inspection of a length of test material, such as a railroad rail, the novelty of the invention is the unique application of electronics and data acquisition techniques. By combining parallel pulse transmission (described below) and sequential virtual apertures (described below) for receiving data it provides a high-speed capability that was not possible with current technology. FIG. 4 shows two samples of defects in a railroad rail (Sample 1 and Sample 2) that are used below to describe the advantages of the invention. As shown in FIG. 4 Sample 1 has more defects than Sample 2.

Figure 5A:
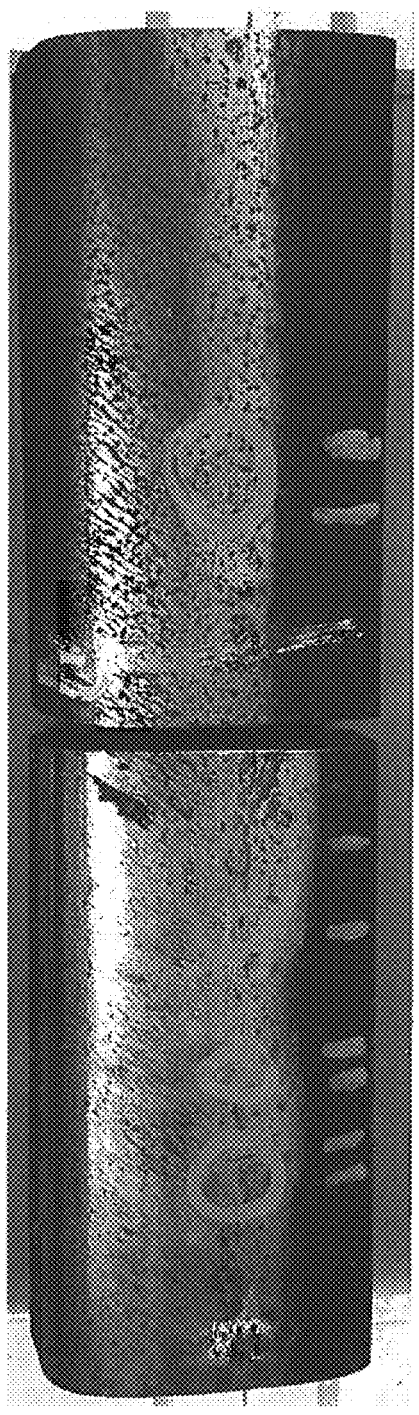
FIGS. 5A and 5B Illustrate the two Samples and a C SCAN using TOF
Figure 5B:
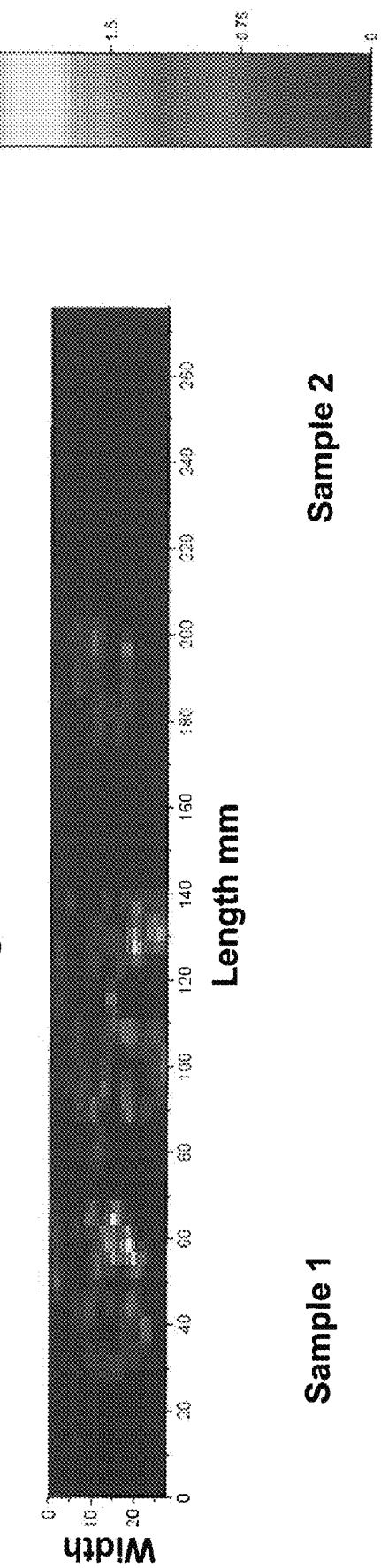
Figure 6A:
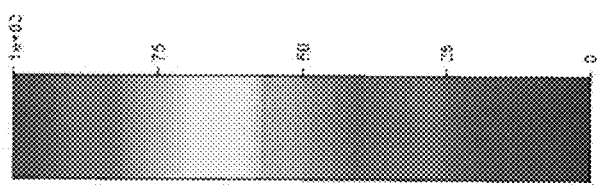
FIGS. 6A and 6B Illustrate the two Samples and a C SCAN using Amplitude
Figure 6A:
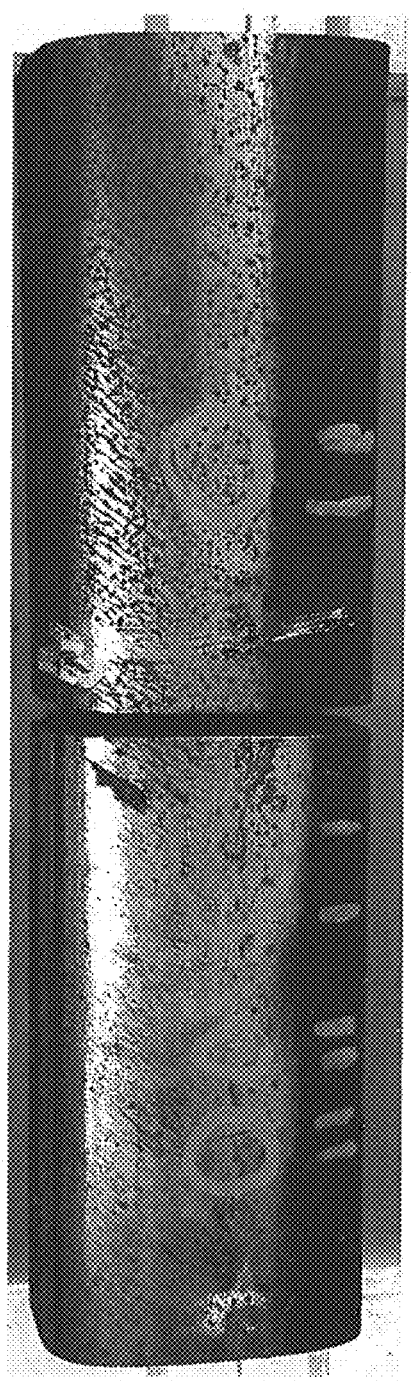
Figure 6B:
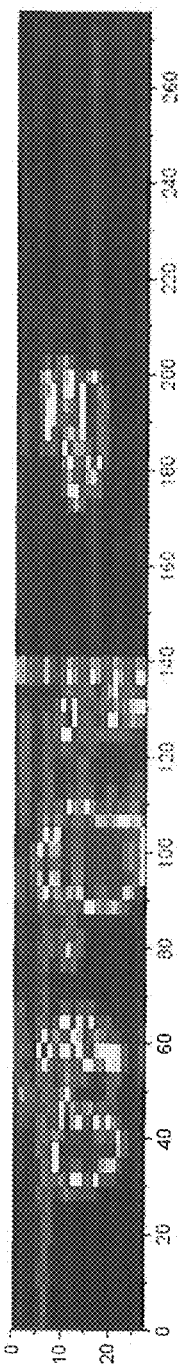
Figure 7:
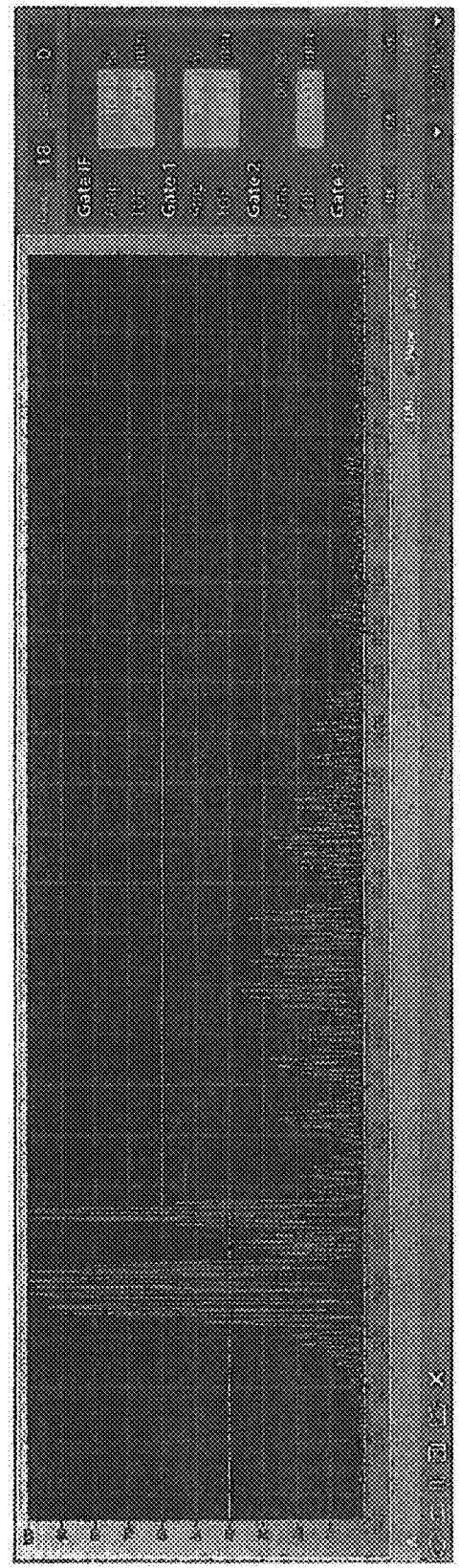
FIG. 7 Illustrates an ASCAN with defect and without defect
Figure 7:
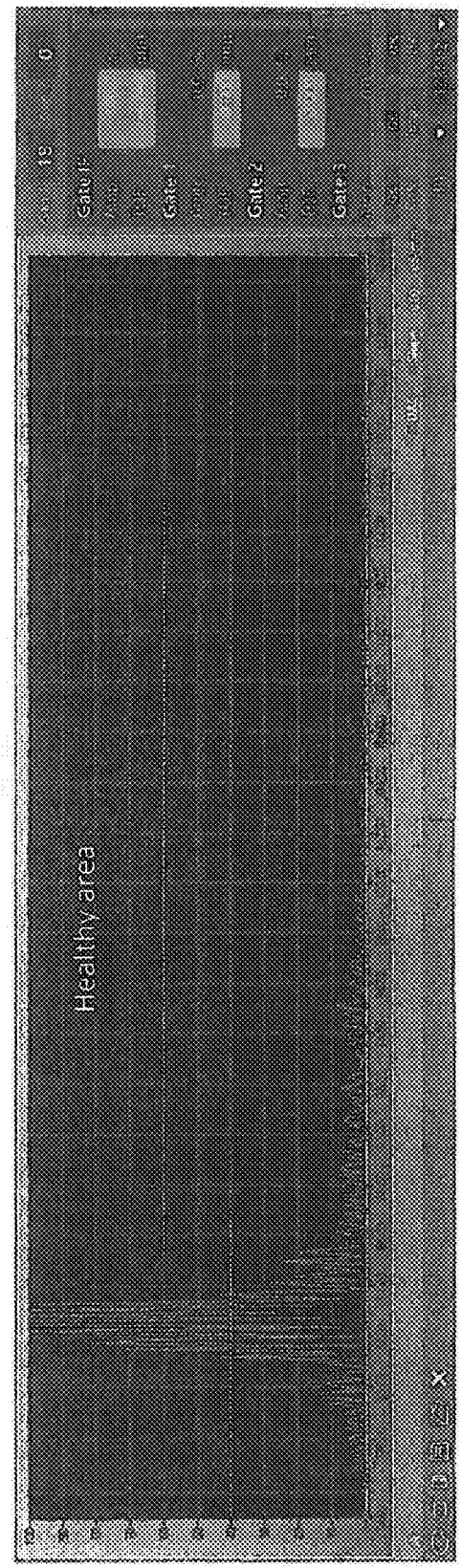

More specifically, for each high-speed scan, and for each echo, the data processing unit has the capability to generate the Time of Flight (TOF), Amplitude and an RF A Scan. The TOF is used to generate a C Scan presentation of a horizontal defect displaying depth and length along the longitudinal position as shown in FIG. 5 for Samples 1 and 2. FIG. 5A shows Sample 1 and Sample 2 also shown in FIG. 4 and FIG. 5B is the CScan presentation. The Amplitude is used to generate a relative C Scan illustrated in FIG. 6 for Samples 1 and 2 that will display a top view of the defect displaying width, length, and severity along the length of the rail. FIG. 6A shows Sample 1 and Sample 2 and FIG. 6B is the C Scan. The RF Scan shown in FIG. 7 illustrates Sample 1 with a defect and an RF Scan without a defect.

In accordance with the invention described herein, FIGS. 1 and 2 illustrate a preferred embodiment for an ultrasonic linear array inspection including wheel 210 perpendicular (its axis) to railroad rail 223 and containing a linear array transducer 220 parallel to the surface of rail head 213. It is to be understood that the linear array shown in FIGS. 1 and 2 is mounted in a testing vehicle that moves longitudinally along the railroad rail. The linear array 220 includes multiple adjacent transducers 225 that electronically scan across head 213 of rail 223 yielding depth and width. The incremental movement as the testing vehicle moves along the rail will provide length information. The multiple transducer elements are contained in a single housing within wheel 210. The number of transducers can vary from 1 to n but typically range from 8 to 64 transducers. For this embodiment, a 32-element linear array, is used. The present invention groups transducer elements, parallel pulses the transmitters and electronically scans across the head utilizing synthetic virtual aperture. This is illustrated in FIG. 3.

Figure 3:
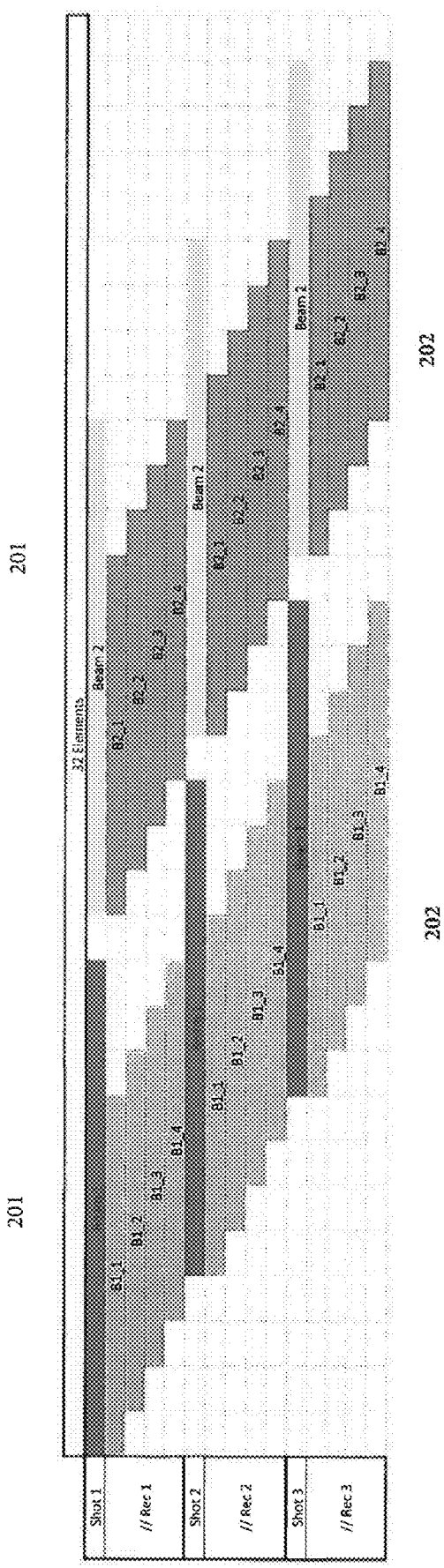

The table in FIG. 3 represent a linear 32 element array along the X axis, the Y Axis represents three sequential parallel pulses (201), each generating 2 beams (Beam 1 and Beam 2) of an 11-element grouping. The left side of FIG. 3 shows when the transducers are activated (Shot 1, Shot 2, Shot 3) and also shows the echoes from each Shot, (Rec.1, Rec.2, Rec. 3). Within each of the 3 parallel pulses (Shot 1, Shot 2, Shot 3) there are 4 sequential virtual apertures in parallel (202, Rec.1,Rec.2, Rec.3) that are used to receive any reflected echoes. The incremental step between each sequential virtual aperture is 1 element. This feature enables the inspection system to collect the equivalent of 24 individual echo's using standard linear array technology in just 3 pulses.

To further clarify, using current conventional linear array technology each incremental pulse of the 24 needed requires approximately 120 microseconds of transmit/receive time or 2,880 microseconds to scan across the entire array. This limits the testing speed to 1.5-2 km/h. Using the new described methodology of using a three-pulse sequence the transmit/receive time will be 120 microseconds multiplied by 3 or approximately a cycle of 360 microseconds for one complete scan across the entire array. The new method described herein significantly increases the testing speed to more than 40 km/h which greatly reduces the testing costs.

FIG. 3 illustrates the combining of the 24 virtual apertures to generate a C Scan presentation where the X axis represents position along the length of the rail and the Y-axis represent the position across the head.

Although a specific embodiment of the invention has been disclosed herein it is to be understood that various modifications can be made to the described embodiment without departing from the scope of the claimed invention, which modification, would be apparent to one skilled in this art area.

The invention claimed is:

1. A system for performing a high speed ultrasonic inspection of railroad rails in order to detect horizontal near surface fractures in a head area of a rail being inspected, which horizontal near surface fractures propagate in a horizontal and longitudinal plane of said rail, said inspection being performed as said inspection system moves along the railroad rails, the system comprising:
   a sensing wheel arranged to roll along the top of the railroad rails being inspected, a linear array generating a full scan per sequential parallel excitation pulse for a plurality of separate groups of transducer elements within said linear array, wherein the plurality of groups of transducer elements are parallel to a surface of the head area of the rails; and
   one or more groups of sequential virtual synthetic apertures in parallel to collect received echo data from said plurality of the separate groups of transducer elements.

2. The system in accordance with claim 1 wherein said virtual synthetic apertures are synthesized into smaller groupings of one or more transducer elements scanning across said head area of said rail.

3. The system in accordance with claim 2 wherein said virtual synthetic apertures are synthesized into small groupings of one or more transducer elements scanning across said head area of said rail and grouping said echo data result to obtain a full scan across said linear array.

4. The system in accordance with claim 1 wherein said system is comprised of a sliding transducer array.

5. The system in accordance with claim 1 which combines echo data results of one or more groupings of said virtual synthetic apertures to generate a TOF Cscan presentation.

6. The system in accordance claim 1 which combines echo data results of one or more groupings of said virtual synthetic apertures to generate an Amplitude Cscan presentation.

7. The system in accordance with claim 1 which combines echo data results of one or more groupings of said virtual synthetic apertures to generate a Ascan presentation.

8. The system in accordance with claim 1 wherein the system locates and classifies defects caused by Rolling Contact Fatigue.

9. The system in accordance with claim 1 wherein the system moves along the rail at a testing speed of more than 40 km/h.

10. The system in accordance with claim 1 wherein the multiple sequential parallel excitation pulses are in a 3 pulse sequence to transmit and receive the echo data.

11. The system in accordance with claim 1 wherein the multiple sequential parallel excitation pulses are in a cycle of 360 microseconds for one complete scan across the entire railroad rail.

* * * * *